United States Patent
Gramnäs

Patent Number: 6,123,732
Date of Patent: Sep. 26, 2000

[54] ADJUSTABLE ADAPTER FOR LOWER LEG PROSTHESIS

[75] Inventor: Finn Gramnäs, Kinna, Sweden

[73] Assignee: Gramtec Innovation AB, Kinna, Sweden

[21] Appl. No.: 08/834,659

[22] Filed: Apr. 11, 1997

Related U.S. Application Data

[63] Continuation-in-part of application No. 08/809,534, Mar. 4, 1997, abandoned.

[51] Int. Cl.[7] .................................................. A61F 2/62
[52] U.S. Cl. ................................................. 623/38; 623/27
[58] Field of Search ........................... 623/27, 28, 30–33, 623/35, 38

[56] References Cited

U.S. PATENT DOCUMENTS

| | | | |
|---|---|---|---|
| 5,013,325 | 5/1991 | Rennerfelt | 623/38 |
| 5,047,063 | 9/1991 | Chen | 623/38 |
| 5,425,782 | 6/1995 | Phillips | 623/38 |
| 5,529,576 | 6/1996 | Lundt et al. | 623/27 |
| 5,545,230 | 8/1996 | Kinsinger et al. | 623/38 |
| 5,545,231 | 8/1996 | Houser | 623/38 |
| 5,549,710 | 8/1996 | Vera et al. | 623/38 |

*Primary Examiner*—Michael J. Milano
*Assistant Examiner*—Tram A. Nguyen
*Attorney, Agent, or Firm*—Gardner, Carton & Douglas

[57] ABSTRACT

An adjustable adapter (13) for lower leg prostheses including an adapter housing (14) attachable to the lower leg prosthesis (2), a spheroidal adapter head (8) rotatable inside the housing (14) and a prosthesis collar attachment member (4) that can be shifted sideways relative to the adapter head (8), which member (4) can be fastened to a prosthesis collar (5) whereby the spheroidal part (12) of the adapter head (8) is on the exterior of the essentially tube shaped adapter head (8) having an internally tube shaped part in which there are parts (26, 27, 28) arranged to allow the prosthesis collar attachment member (4) to be shifted sideways.

19 Claims, 7 Drawing Sheets

ADJUSTABLE ADAPTER FOR LOWER LEG PROSTHESIS

CROSS REFERENCES TO RELATED APPLICATIONS

This application is a Continuation-In-Part of U.S. patent application Ser. No. 08/809,534, filed Mar. 4, 1997, now abandoned.

BACKGROUND OF THE INVENTION

1. Field of the Invention

The present invention pertains to an adjustable adapter for lower leg prostheses having a spheroidal adapter head mounted within an adapter housing.

Prostheses for the knee, lower leg or foot are normally fastened to the bearer's bone using a prosthesis collar. To make the prosthesis adjustable at the desired angle and to make it possible to adjust it transversely to the prosthesis collar adapters for that purpose have previously been proposed.

2. Description of the Related Art

SE-B-8602143-3 describes a lower leg prosthesis equipped with such an adapter which includes a prosthesis collar attachment member for attachment to the lower collar of the prosthesis. On the side facing the prosthesis collar the prosthesis collar attachment member is screwed to an adapter element including a little hemisphere around the screw shaft, which hemisphere is made rotatable against a corresponding spheroidal inner surface in an adapter housing which is attached to a lower leg prosthesis at its opposite end. At a distance from the hemisphere there is a concentrically attached disc against which the prosthesis collar attachment abuts. Further, there are external bosses on the adapter housing equipped with threaded penetrating holes at an angle to the central axis in which pinning screws can be screwed in from below so that their front ends press against the disc attached to the hemisphere thus pressing the adapter housing to different angular positions relative to the adapter housing. The prosthesis collar attachment element has a penetrating hole of significantly greater dimensions than the fastening screws in it whereby using a washer it is possible to attach the prosthesis collar attachment element in different sideways adjustable positions relative to the adapter housing. Using this design it is possible to achieve different angular positions without detaching the prosthesis, but because of the small radius of the sphere the angular variation is relatively limited. At the same time a sideways adjustment can be achieved but for this it is necessary that the whole prosthesis including the prosthesis collar be detached to reach the side adjustment screws, all of which makes fitting more difficult.

SUMMARY OF THE INVENTION

Other types of similar adapters have the two adjustment functions separated to such a degree that the designs are large and unwieldy.

The purpose of the present invention is to provide an adjustable adapter for a lower leg prosthesis for which the above disadvantages are essentially eliminated, which has been achieved by giving the adapter the characteristics described.

BRIEF DESCRIPTION OF THE DRAWINGS

In the following the invention will be described in greater detail with reference to the exemplifications illustrated schematically in the attached figures.

DESCRIPTION OF THE PREFERRED EMBODIMENTS

Figure 1:
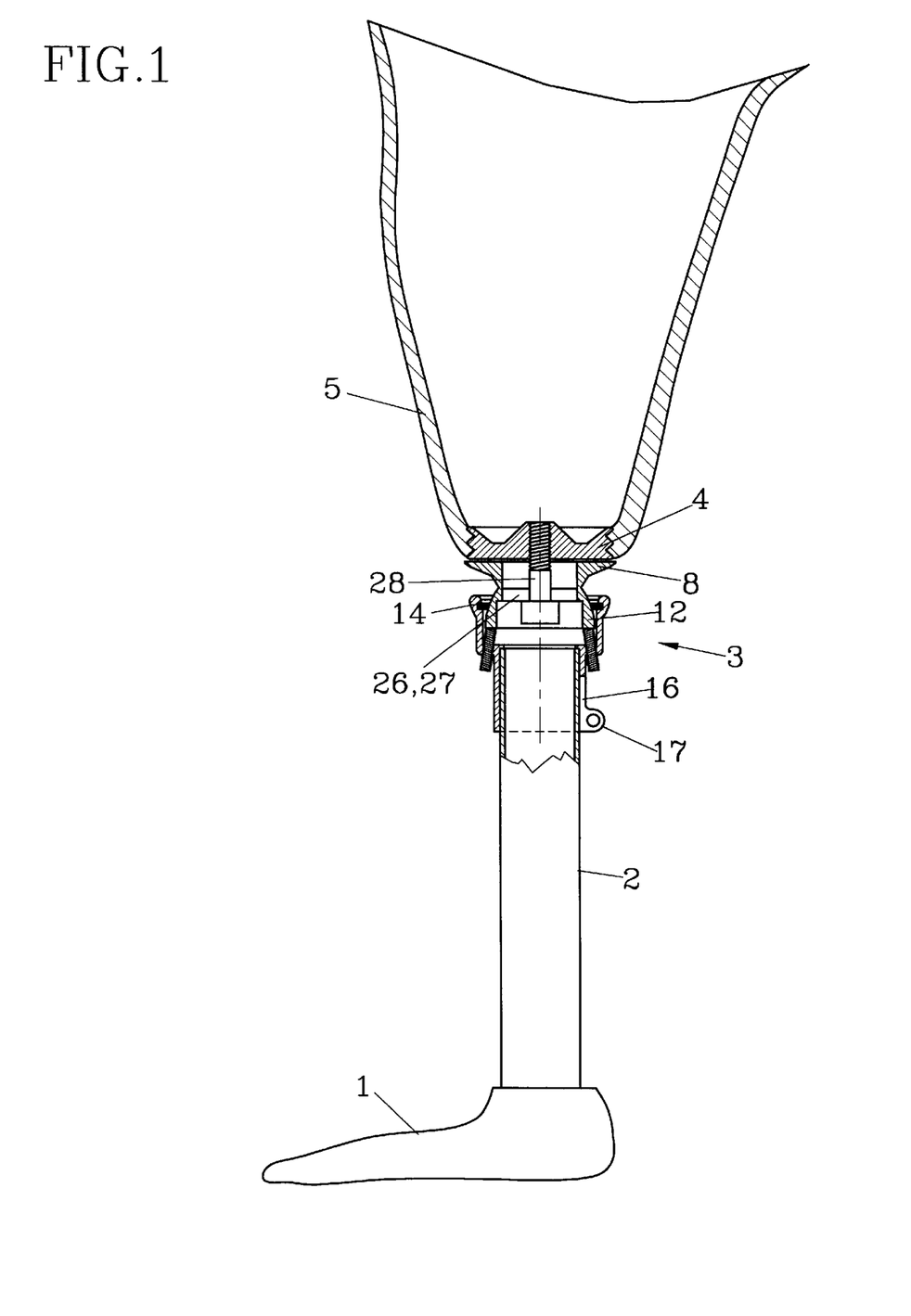
FIG. 1 shows an exemplification of a lower leg prosthesis with included adapter according to the present invention in schematic cross section from the side.

In FIG. 1 a prosthesis foot 1 with an adjacent long leg like element, preferably a tube 2, appropriately made of aluminum or another light strong material, is shown schematically. On the end facing away from the prosthesis foot the leg like element 2 is attached to an adapter 3 according to the invention, which is affixed to a prosthesis collar 5 using a prosthesis collar attachment member 4 that can be adjusted relative to the attachment end of the leg like element.

Figure 2:
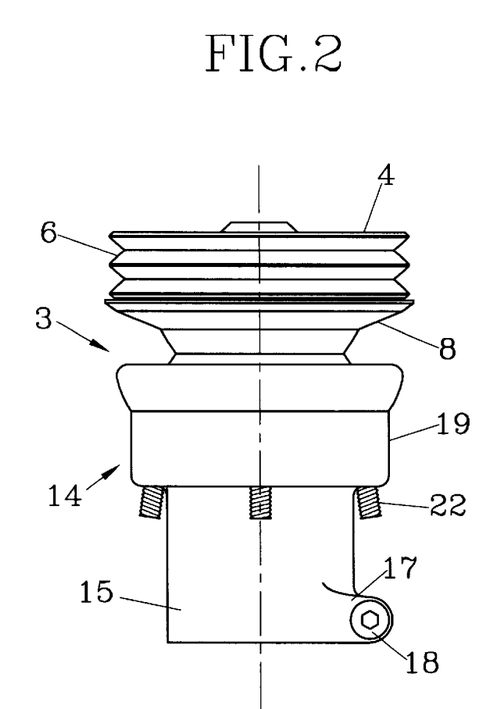
FIG. 2 is a side view of the adapter according to FIG. 1.
Figure 3:
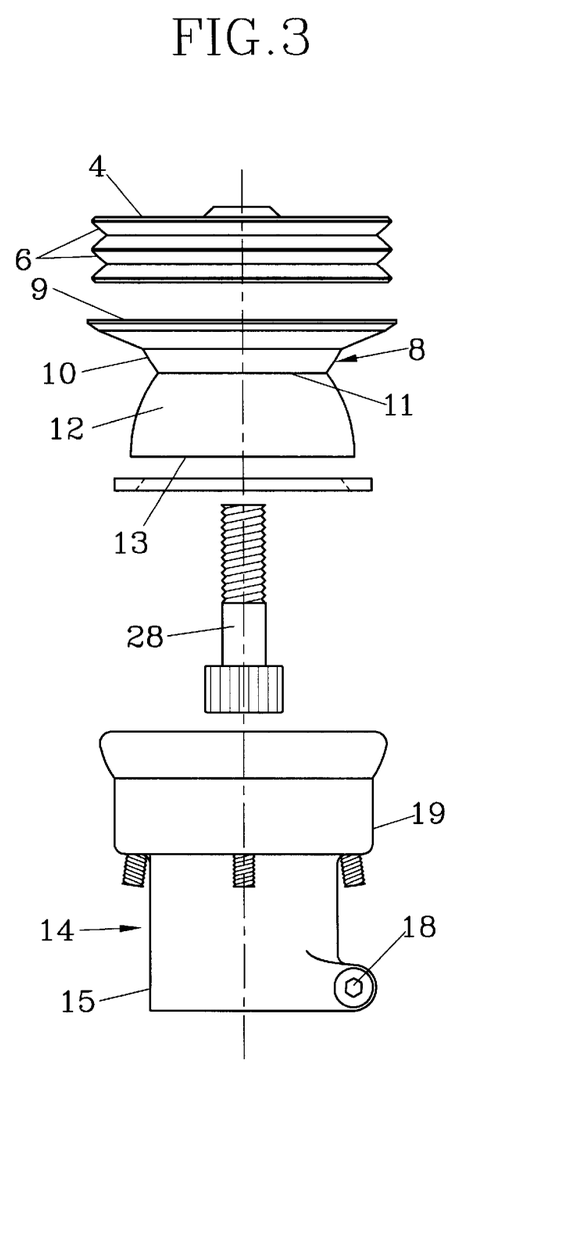
FIG. 3 shows a enlarged view from the side of the adapter according to FIG. 2.
Figure 4:
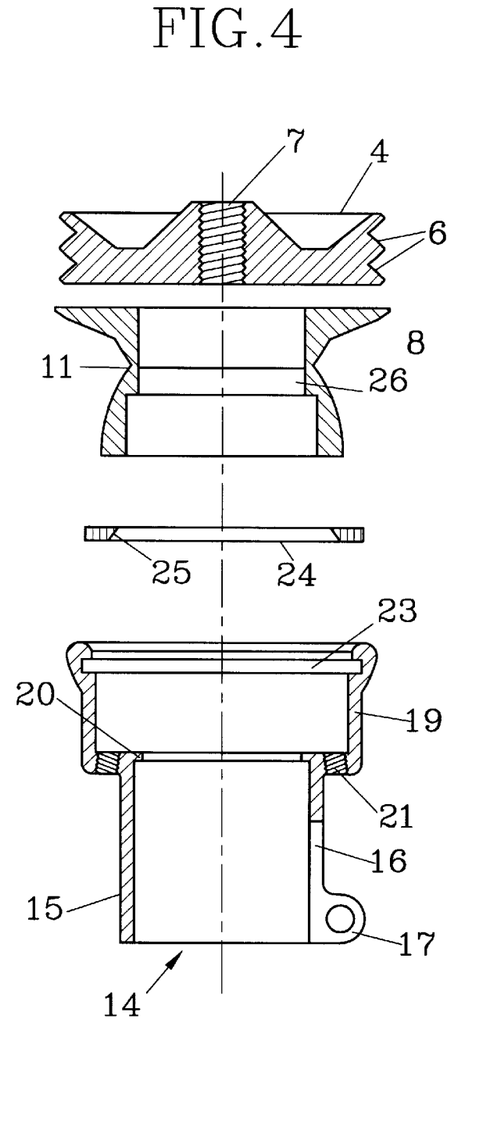
FIG. 4 is a enlarged view corresponding to FIG. 3 which shows the adapter's most important parts in section.

FIGS. 2 to 4 show the adapter according to FIG. 1 on a larger scale from the side in a enlarged view and in a enlarged view in section, respectively. It is clear from the figures that the previously mentioned prosthesis collar attachment member 4 is included in the adapter 3, which member in the shown design consists of a circular disc with external grooves 6 which facilitate attachment of the member 4 to the prosthesis collar. In the shown design the disc has a central threaded hole 7 (see FIG. 1 and FIG. 4). For reasons to be given shortly, the prosthesis collar attachment member 4 or the central hole 7 can include an oblong hole (not shown). Further included in the adapter 3 is an adapter head 8 consisting of a collar with a circular ring shaped end surface 9 facing toward the prosthesis collar attachment member 4 and pressing against it. On the end surface 9 there is a conical section 10 which from a midline 11 is transformed to an essentially spherical concentric form 12. The spherical part 12 of the adapter ends in a circular ring shaped surface 13 which is mainly parallel to the adapter head's opposite end surface 9. Further there is an adapter housing 14 which includes a tube shaped section 15 designed to be attached to the tube like structure, for which purpose the under part of which has a slit 16 (see for example FIG. 1) while the material on either side of the slit 16 has attachment members 17 for a connector 18, for example a bolt, with which the end of the tube shaped part, which is somewhat elastic because of the slit, can be fastened to the upper end of the tube like structure 2. On the end facing away from the slit part of the tube shaped section 15 of the adapter housing 14 the tube like structure meets a bowl shaped sleeve 19 concentric with the tube shaped section 15 and of a larger diameter than the latter. The sleeve 19 and the tube shaped section meet each other at a ring shaped connector 20 attached essentially perpendicular to the adapter housing's central axis. Through that connector extend a number, preferably four, equidistant angled threaded holes 21 designed for pinning screws 22 or the like. On the end of the sleeve 19 away from the tube shaped section 15 the sleeve has an encircling groove for a lock washer 24 with a hole 25 preferably of a form complementary to that of the spheroidal form 12 and with a contact line which, when assembled symmetrically, is in the middle of the spheroidal surface 12, that is, with its smaller opening turned axially out from the sleeve part when assembled, so that because of the increasing diameter of the spheroidal part 12 in the downward direction, after insertion into the sleeve 19 and attachment of the lock washer 24 the adapter head cannot be extracted from the sleeve but using the pinning screws it can be locked at a desired angle. The lock washer 24 is preferably equipped with a slit (not shown) which facilitates its insertion into the groove 23.

The inner diameter of the opening in the sleeve 19 is somewhat larger that the outer diameter of the end surface 13 of the adapter head's spheroidal part 12 so that it fits into the sleeve and at its ring shaped end surface presses against the pinning screws 22 in the adapter housing 14, as for instance is seen in FIG. 1 where the adapter head's middle part 11 is above the sleeve 19. By inserting the lock washer 24 into the groove 23 in the adapter housing 24 after inserting the adapter head 8 into it the lock washer prevents the adapter head from being withdrawn from the sleeve 19 while at the same time because of the spheroidal part 12 the adapter head can be set at an angle relative to the lengthwise axis of the adapter housing. The angled hole 25 in the lock washer 24 thus also contributes to making that angular positioning smooth and frictionless without scratching contact between the spheroidal part 12 and the edge of the hole 25.

Figure 5:
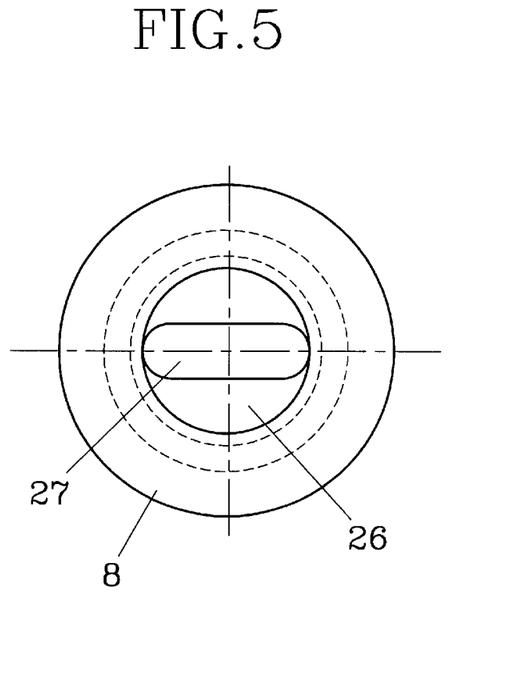
FIG. 5 shows an adapter head included in the adapter according to the invention in a view from above.

In FIG. 4 it is clear from the section of the adapter head 8 that approximately at the level of the external middle part 11 it has an interior partition which has a penetrating oval hole 27 placed symmetrically on the center of the interior partition 26, as is clear from FIG. 5 in which the adapter head is shown in a top view.

For internal connection between the prosthesis collar attachment member 4 and the adapter head 8 a connector 28 is used, in the example shown in the form of a bolt through the oval hole 27 in the adapter head with its threaded shaft screwed into the threaded hole 7 in the prosthesis collar attachment member 4. Because the connector 28 has a part that cannot go through the oval hole 27, that is, in the present case the head of the bolt is larger in diameter that the width of the hole 27, the connector can be applied without its head going through the hole 27. Because that hole is oval it is still possible to attach the connector 28 in different positions along the length of the hole making adjustment along the length of the hole possible. With the alternative design of the prosthesis collar attachment member with an oblong hole instead of the centered hole 7 using a slide groove (not shown) in the prosthesis collar attachment member it is possible to use a nut as the connector 28 which is self locking along the length of the hole in the prosthesis collar attachment member 4. Thus the extent of the adjustability of the prosthesis adapter is further increased.

In FIGS. 6a–g the adapter 3 according to the invention is shown in section in different adjustment positions between the prosthesis collar attachment member 4 and the adapter head 8 and between the adapter head 8 and the adapter housing 14. In this way a great variety of adjustment positions is made possible which further can be realized with an adapter that can be of a low and particularly compact design because of the large spheroidal part of the adapter head in the sleeve of the adapter housing.

Figure 6A:
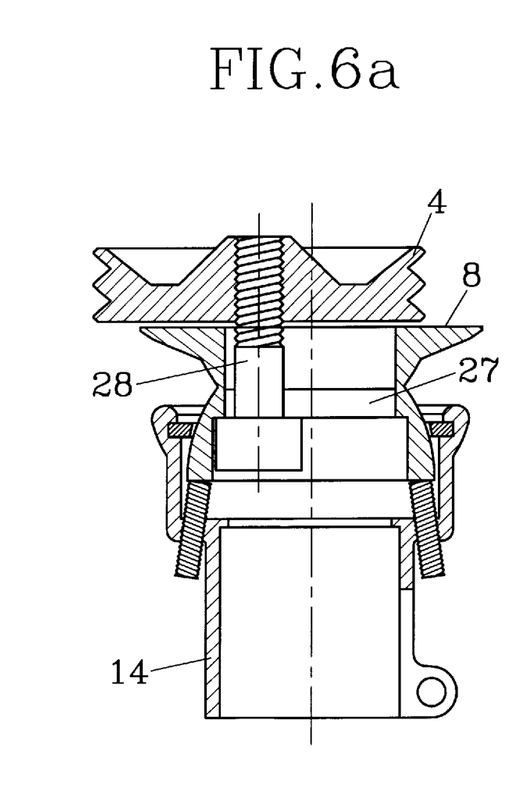
FIGS. 6a–g show different adjustments of the adapter according to the invention in side views seen in section.

Thus FIG. 6a shows how the adapter head 8 is adjusted so that its center line forms a direct extension of the center line of the adapter housing 14, that is, no angular displacement of the center line results. On the other hand the axis of the prosthesis collar attachment member 4 is shifted parallel with respect to the center line of the adapter head 8 and therefore to the center axis of the adapter housing. This has been achieved by shifting the connector 28 to its position, in the figure, furthest to the left in the oval hole 27 in the adapter head.

Figure 6B:
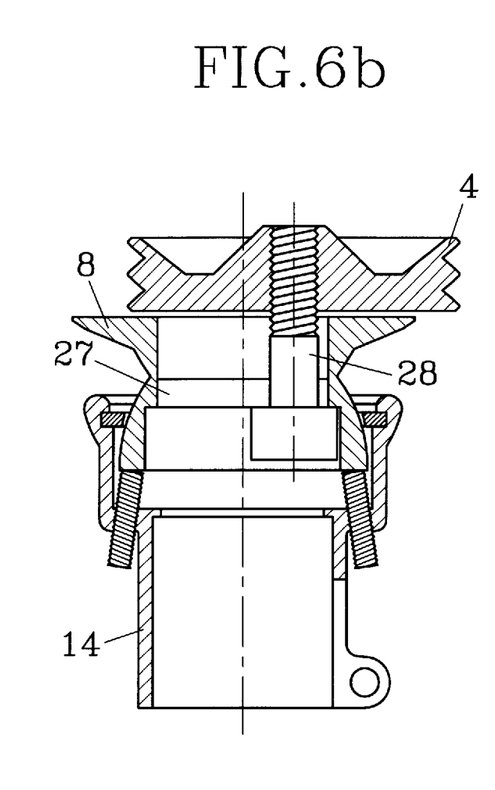
Figure 6C:
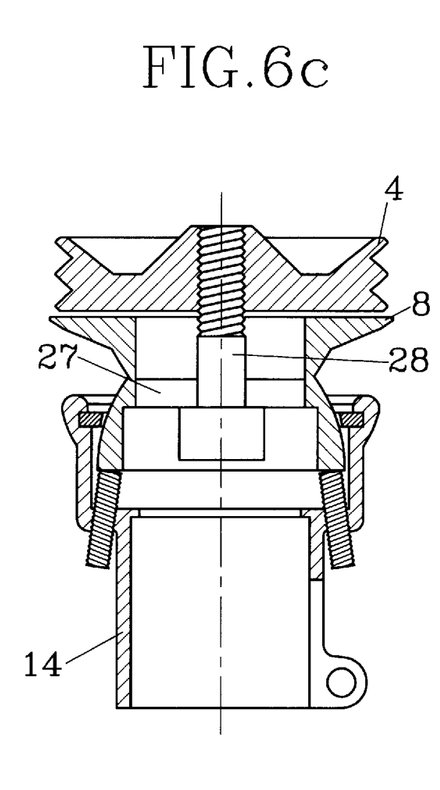

Also in FIGS. 6b and 6c the adapter head 8 and the adapter housing are arranged with no angle between them while the prosthesis collar attachment member 4 in FIG. 6b is placed at its other maximally shifted end position and the connector 28 in FIG. 6c is placed centrally in the hole 27 so that the center line of the prosthesis collar attachment member 4 not only is parallel to but also coincides with the center line of the adapter housing 14 and of the adapter head 8.

Figure 6D:
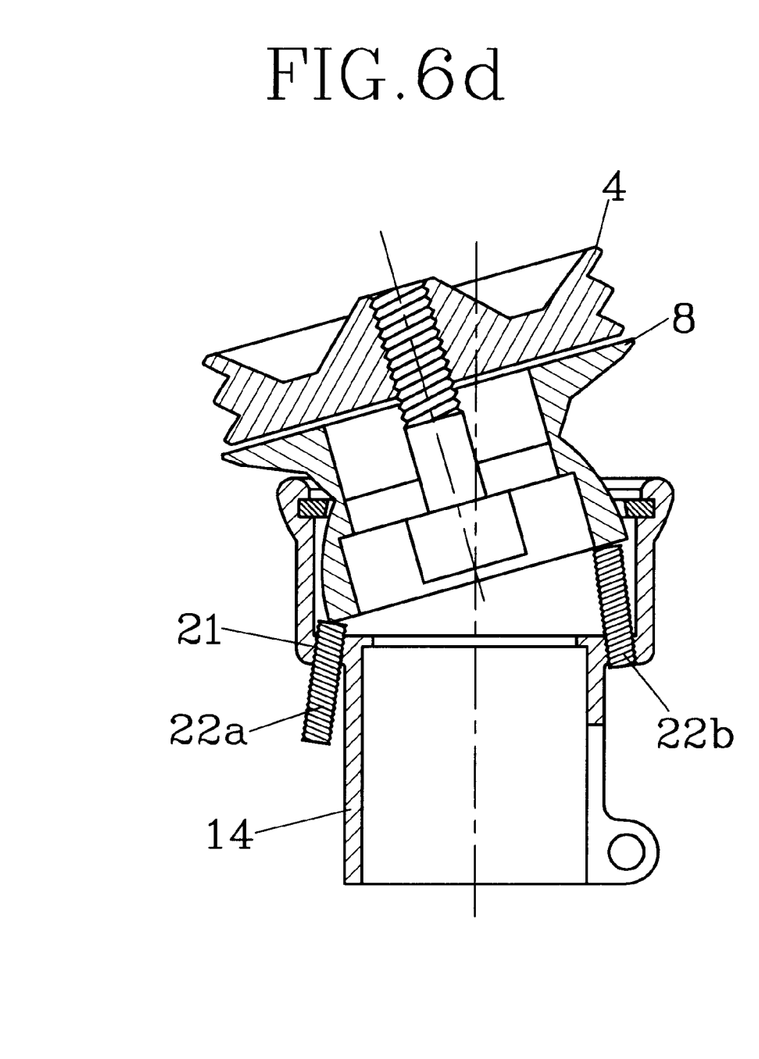
Figure 6E:
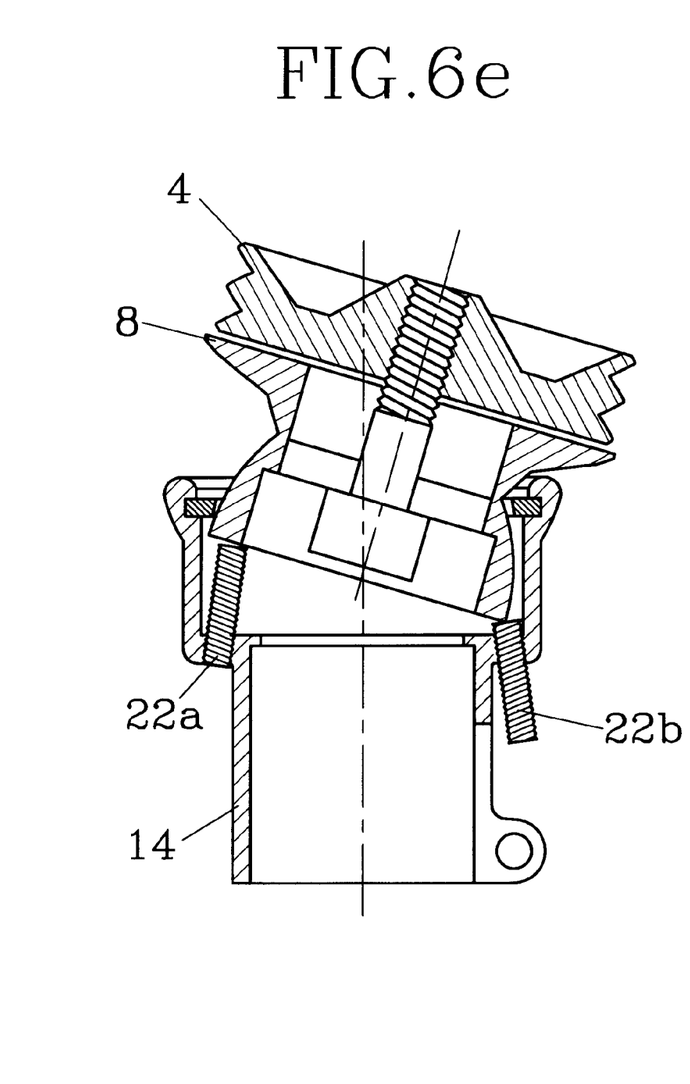

In FIG. 6d and 6e is shown how the prosthesis collar attachment member 4 and the adapter head 8 are in the same relative position as shown in FIG. 6c but where in both cases the adapter head 8 has been rotated in its seat in the adapter housing 14 relative to the latter so that their respective center lines form an angle. This relative angular adjustment has been achieved in FIG. 6d by unscrewing the front pinning screw 22a almost completely from its hole 21 while the back screw has been screwed in to a corresponding extent. Thus the back screw 22b in the figure lifts the right part of the adapter head 8 which, because of the spheroidal external surface placed inside the sleeve part of the adapter housing, tips in the sleeve and rests at an angle to the left in the figure with its own center axis and the prosthesis collar attachment member center axis maximally angled to the left relative to the center axis of the adapter housing.

In FIG. 6e the situation is the reverse, that is, the front pinning screw 22a has been screwed in maximally while the back one 22b has been screwed out. The angle of the coincident center lines for the prosthesis collar attachment member 4 and the adapter head 8 relative to the center axis of the adapter head 8 is as great as is the case in FIG. 6d but in this case the center line of the prosthesis collar attachment member 4 and the adapter head 8 is angled to the right relative to the center line of the adapter housing.

Figure 6F:
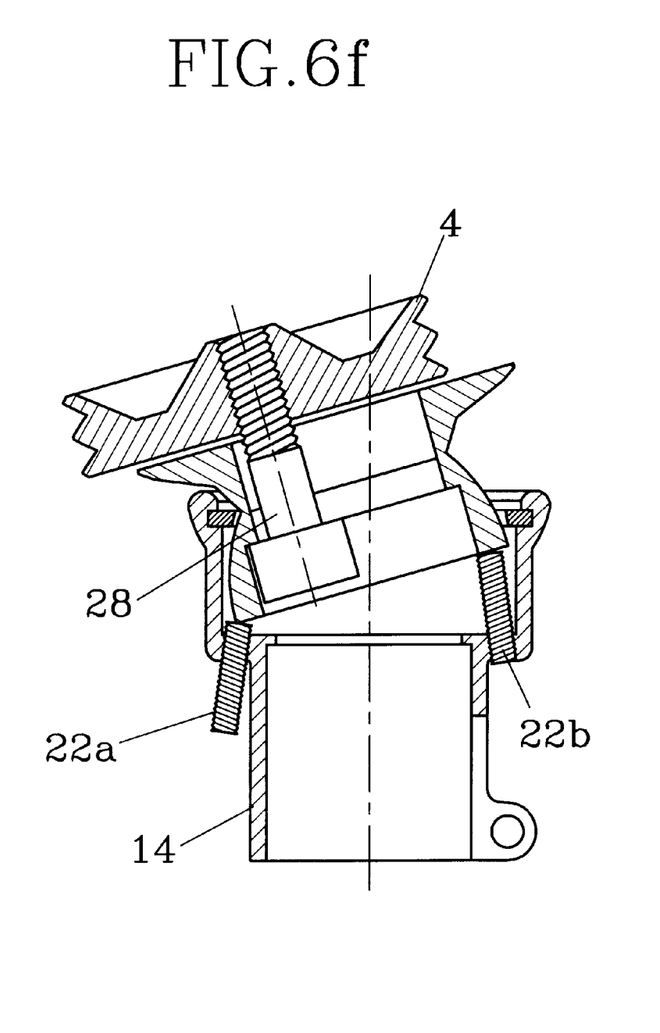
Figure 6G:
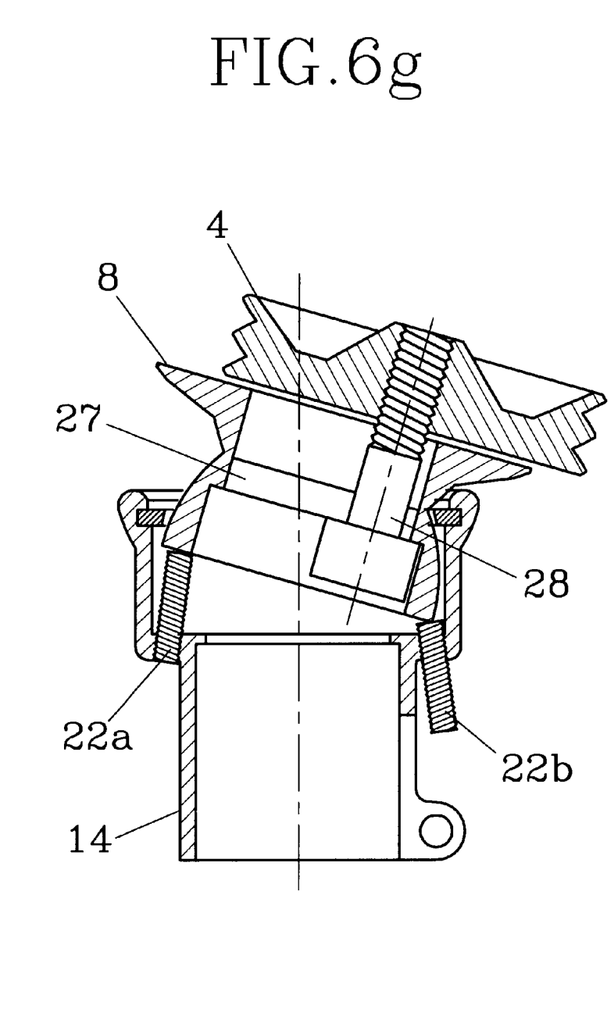

In FIG. 6f and 6g are finally shown two positions in which the adapter housing 14 and the adapter head 8 are angled relative to each other in the same way is in FIGS. 6d and 6e where the angular adjustment has been made in the same way as in the two previously described cases. In addition the center axes of the prosthesis collar attachment member 4 and the adapter head 8 in the two FIGS. 6f and 6g are shifted parallel relative to each other in the same way and by the same means as in FIGS. 6a and 6b, respectively.

For simplicity in FIGS. 6d to 6g how the adapter head 8 and the adapter housing 14 have been angled relative to each other has been shown only in the plane of the paper where only the front and back pinning screws 22a and 22b, respectively, have been screwed into or out from their neutral positions. Because the adapter housing 14 can also have more equidistant adjustment screws 22, preferably four, it is assumed that the angular adjustment can also be achieved in a plane perpendicular to the plane of the paper and/or in a combination of the planes, that is, the angle between the adapter housing and the adapter head, and thereby between the lower leg tube and the prosthesis collar attachment member 4, can be adjusted as desired to all angular positions while at the same time a sideways shift of the lower leg tube 2 and the prosthesis collar attachment member 4 can be obtained. Because the adapter head 8 has no fixed position relative to the adapter housing 14 the adapter head can also be rotated relative to the adapter housing 14 so that a parallel shift of the center axes of the prosthesis collar attachment member 4 and the adapter head 8 can be achieved in any desired direction perpendicular to the center axis of the adapter housing.

Using the design's large spheroidal adapter housing, which can be locked in position relative to the adapter housing in the way described and which has a built in sideways shift function, an extremely compact and therefore space saving design and a total adjustability for an externally applied knee/lower leg/foot prosthesis is achieved.

Figure 7:
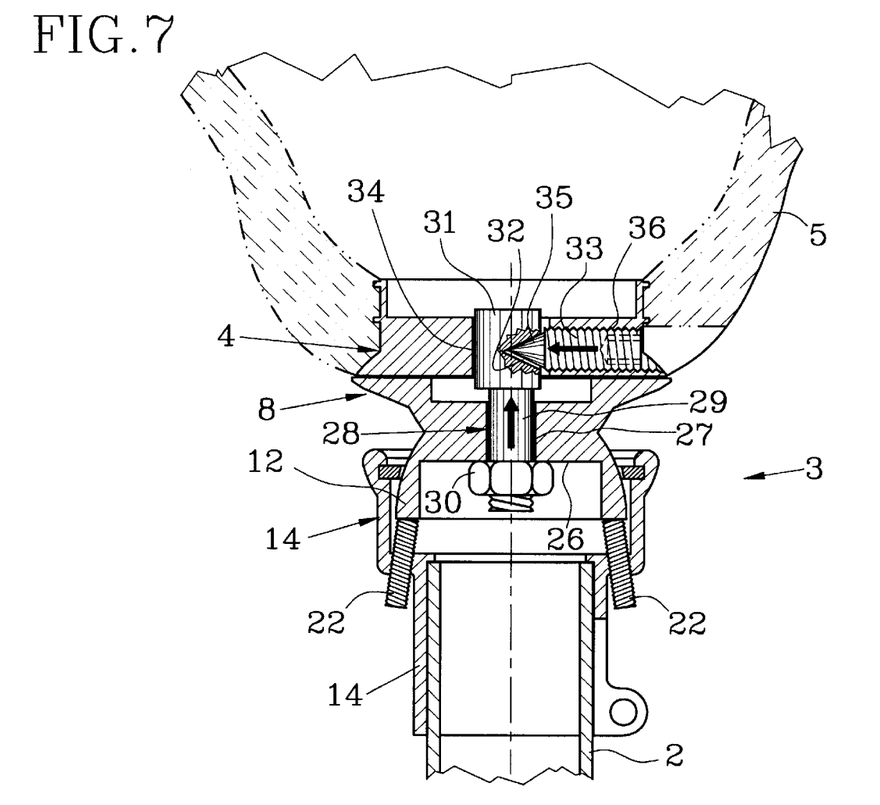
FIG. 7 shows a section through a modified embodiment of the adapter according to the invention in a locked position.
Figure 8:
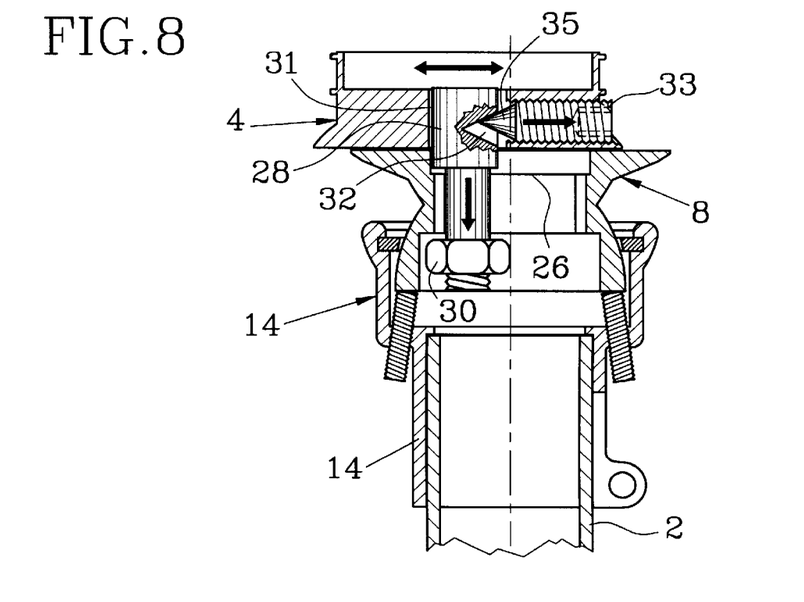
FIG. 8 shows the adapter according to FIG. 7 in a released position.

The above described sideways displacement function of the adapter is prevented by tightening the screw, which is accessible from inside the adapter housing 14. This means that the lower leg prosthesis 2 must be removed when an adjustment is to be made. In the embodiment shown in FIGS. 7 and 8 the adjustment can be made without needing to remove the lower leg prosthesis. For this purpose the connector 28, i.e. the screw is provided with a cylindric head 31, which is axially displaceable in a bore 34 in the prosthesis collar attachment means 4. The screw head 31 is provided with a radial conical recess 32, which with respect to the screw axle makes an inclined contact surface. In the prosthesis collar attachment means 4 there is arranged a maneuver member 33 in the form of a stop screw, the inner end of which is designed with a conical tip 35. This is intended to cooperate with the conical recess in such a way that when the stop screw is somewhat unscrewed from its threaded hole 36, the connector 28 can be axially displaced, so that the adapter housing 14 becomes moveable transversally with respect to the prosthesis collar attachment means, as can be seen from FIG. 8. After adjusting these parts relative to each other the stop screw 33 can be screwed into the conical recess in the locking member, at which the conical tip 35 cooperates with the inclined contact surface of the recess 32 and lifts the screw so much that the nut 30 will be brought in contact with the partition wall 26, as can be seen from FIG. 7.

The invention is not limited to the shown and described exemplifications but instead modifications are possible within the frame of the following patent claims.

What is claimed is:

1. An adjustable adapter for a lower leg prosthesis, the adapter comprising:
    an adapter housing having an open upper end and a lower end, wherein the adapter housing is attached to the lower leg prosthesis at the lower end;
    an adapter head having a first end, a part-spheroidal portion at a second end, and an oval hole formed in an interior partition that is between the first end and the spheroidal portion, wherein the spheroidal portion is movably mounted within the open upper end of the adapter housing so that the adapter housing and adapter head form an integrated unit with the first end of the adapter head being distal to the lower end of the adapter housing;
    angular adjustment means movably connected to the adapter housing to engage with the spheroidal portion wherein the angular adjustment means are settable in different positions to adjust the angular relationship between the adapter housing and the spheroidal portion;
    a prosthesis collar attachment member having a first end and a second end, wherein the first end is connected to a prosthesis collar and the second end is connected to the adapter head; and
    a locking member which extends through the oval hole of the adapter head into the prosthesis collar attachment member so that the prosthesis collar attachment member is sideways displaceable relative to the adapter head by movement of the adjustment means.

2. The adjustable adapter according to claim 1 wherein the adapter housing comprising a sleeve portion at the upper end, wherein the spheroidal portion is movably mounted in the sleeve portion so that center axes of the adapter housing and the adapter head can be angled relative to each other.

3. The adjustable adapter according to claim 2 further comprising an openable washer attached to the sleeve to retain at least a portion of the spheroidal portion to the adapter housing wherein the spheroidal portion is pressed in contact against the openable washer to maintain the adapter head in a position relative the prosthesis collar attachment member.

4. The adjustable adapter according to claim 2 wherein the adapter housing further comprising:
    a tube portion between the sleeve and the lower end wherein the tube attaches to the lower leg prosthesis, and
    a flange at the transition between the sleeve and the tube wherein the flange having holes through which the angular adjustment means movably connect to the adapter housing.

5. The adjustable adapter according to claim 1 wherein the adapter head further comprises a plane ring shaped surface at the first end to connect to the prosthesis collar attachment member, a conically divergent part extending from the plane ring shaped surface towards a midline and wherein the midline transforms into the spheroidal portion such that a spheroidal surface faces the first end.

6. The adjustable adapter according to claim 5 wherein the spheroidal portion ends in ring-shaped end surface which is parallel to the plane ring-shaped surface and the angular adjustment means act upon the ring-shaped end surface of the spheroidal portion.

7. An adjustable adapter for a lower leg prosthesis, the adapter comprising:
    an adapter housing having an open upper end, a lower end, and an internal groove formed towards the upper open end wherein the adapter housing is attached to the lower leg prosthesis at the lower end;
    an adapter head having a first end, a part-spheroidal portion towards a second end and a midline between the first end and the spheroidal portion, wherein the spheroidal portion is movably mounted within the open upper end of the adapter housing so that the adapter housing and the adapter head form an integrated unit with the first end of the adapter head being distal to the lower end of the adapter housing with the adapter head being retained in the adapter housing by an openable washer that is placed around the midline and fits into the internal groove;
    angular adjustment means movably connected to the adapter housing to engage with the spheroidal portion wherein the angular adjustment means are settable in different positions to adjust the angular relationship between the adapter housing and the spheroidal portion;
    a prosthesis collar attachment member having a first end and a second end wherein the second end is connected to the adapter head by a locking member so that the prosthesis collar attachment member is sideways displaceable relative the adapter head by moving the adjustment means so that the spheroidal portion is pressed in contact against the openable washer to maintain the adapter head in a position relative the prosthesis collar attachment member.

8. The adjustable adapter according to claim 7 wherein the adapter housing comprising a sleeve portion at the upper end wherein the spheroidal portion is mounted in the sleeve portion so that center axes of the adapter housing and the adapter head can be angled relative to each other.

9. The adjustable adapter according to claim 8 further comprising an openable washer attached to the sleeve to retain at least a portion of the spheroidal portion to the adapter housing.

10. The adjustable adapter according to claim 8 wherein the adapter housing further comprising:
 a tube portion between the sleeve and the lower end wherein the tube attaches the lower leg prosthesis; and
 a flange at the transition between the sleeve and the tube wherein the flange having holes through which the angular adjustment means movably connect to the adapter housing.

11. The adjustable adapter according to claim 7 wherein the adapter head further comprises a plane ring-shaped surface at the first end to connect to the prosthesis collar attachment member and wherein the midline transforms into the spheroidal portion such that a spheroidal surface faces the first end.

12. The adjustable adapter according to claim 11 wherein the spheroidal portion ends in ring-shaped end surface which is parallel to the plane ring-shaped surface and the angular adjustment means act upon the ring-shaped end surface of the spheroidal portion.

13. An adjustable adapter for a lower leg prosthesis, the adapter comprising:
 an adapter housing having an open upper end, a lower end wherein the adapter housing is attached to the lower leg prosthesis at the lower end;
 an adapter head having a first end, a part-spheroidal portion at a second end wherein the spheroidal portion is movably mounted within the open upper end of the adapter housing so that the adapter housing and adapter head form an integrated unit with the first end of the adapter head being distal to the lower end of the adapter housing;
 angular adjustment means movably connected to the adapter housing to engage with the spheroidal portion wherein the angular adjustment means are settable in different positions to adjust the angular relationship between the adapter housing and the spheroidal portion;
 a prosthesis collar attachment member having a first end, a second end and a hole formed between the first and second ends, wherein the first end is connected to a prosthesis collar and the second end is connected to the adapter head;
 a locking member having a head end with a bore conical recess formed therein, wherein the locking member extends through the prosthesis collar attachment member into the adapter head so that the conical recess aligns with the bore; and
 a maneuver member having a conical tip, wherein the maneuver member is movable within the bore and the conical recess so that the prosthesis collar attachment member is sideways displaceable relative to the adapter head.

14. The adjustable adapter according to claim 13 wherein the locking member further comprising a nut to engage an end of the lock member distal the head end.

15. The adjustable adapter according to claim 13 wherein the adapter housing comprising a sleeve portion at the upper end, wherein the spheroidal portion is movably mounted in the sleeve portion so that center axes of the adapter housing and the adapter head can be angled relative to each other.

16. The adjustable adapter according to claim 15 further comprising an openable washer attached to the sleeve to retain at least a portion of the spheroidal portion to the adapter housing.

17. The adjustable adapter according to claim 15 wherein the adapter housing further comprising:
 a tube portion between the sleeve and the lower end wherein the tube attaches to the lower leg prosthesis; and
 a flange at the transition between the sleeve and the tube wherein the flange having holes through which the angular adjustment means movably connect to the adapter housing.

18. The adjustable adapter according to claim 13 wherein the adapter head further comprises a plane ring-shaped surface at the first end to connect to the prosthesis collar attachment member, a conically divergent part extending from the plane ring-shaped surface towards a midline and wherein the midline transforms into the spheroidal portion such that a spheroidal surface faces the first end.

19. The adjustable adapter according to claim 18 wherein the spheroidal portion ends in ring-shaped end surface which is parallel to the plane ring-shaped surface and the angular adjustment means act upon the ring-shaped end surface of the spheroidal portion.

* * * * *